United States Patent
Downey et al.

(10) Patent No.: US 11,974,856 B2
(45) Date of Patent: May 7, 2024

(54) WEARABLE SENSOR AND METHOD OF FORMING THEREOF

(71) Applicant: Analog Devices International Unlimited Company, Limerick (IE)

(72) Inventors: Fergus Downey, Oranmore (IE); Donal McAuliffe, Raheen (IE)

(73) Assignee: Analog Devices International Unlimited Company, Limerick (IE)

( * ) Notice: Subject to any disclaimer, the term of this patent is extended or adjusted under 35 U.S.C. 154(b) by 686 days.

(21) Appl. No.: 17/064,587

(22) Filed: Oct. 6, 2020

(65) Prior Publication Data
US 2021/0153802 A1 May 27, 2021

Related U.S. Application Data

(60) Provisional application No. 62/939,805, filed on Nov. 25, 2019.

(51) Int. Cl.
*A61B 5/00* (2006.01)
*A61B 5/01* (2006.01)
(Continued)

(52) U.S. Cl.
CPC .............. *A61B 5/441* (2013.01); *A61B 5/002* (2013.01); *A61B 5/01* (2013.01); *A61B 5/0537* (2013.01);
(Continued)

(58) Field of Classification Search
CPC .......... A61B 5/441; A61B 5/002; A61B 5/01; A61B 5/0537; A61B 5/14539;
(Continued)

(56) References Cited

U.S. PATENT DOCUMENTS 4,860,753 A 11/1989 Amerena
6,256,523 B1 * 7/2001 Diab .................. A61B 5/14552
600/323
(Continued)

FOREIGN PATENT DOCUMENTS

CN 203369905 1/2014
DE 1598910 A1 5/1970
(Continued)

OTHER PUBLICATIONS

Secor et al., "High-Performance Inkjet-Printed Indium-Gallium-Zinc-Oxide Transisotrs Enabled by Embedded, Chemically Stable Graphene Electrodes", Applied Materials & Interfaces, 8, 17428-17434, published Jun. 21, 2016 (Year: 2016).*
(Continued)

*Primary Examiner* — Matthew Kremer
*Assistant Examiner* — Jonathan Drew Moroneso
(74) *Attorney, Agent, or Firm* — ArentFox Schiff LLP (57) ABSTRACT

A wearable sensor for measuring a parameter of human skin is described and includes a flexible body comprising sensor components formed on, adjacent or within the flexible body and configured to generate a first signal indicative of the parameter of human skin; microfabricated processing circuitry formed within the flexible body, coupled to the sensor components and configured to process the first signal to produce a second signal; and an antenna, formed on, adjacent or within the flexible body, the antenna being coupled to the processing circuitry and configured to transmit the second signal to an external device.

14 Claims, 9 Drawing Sheets

(51) Int. Cl.
*A61B 5/0537* (2021.01)
*A61B 5/145* (2006.01)
*G01N 27/22* (2006.01)
*G01N 33/483* (2006.01)

(52) U.S. Cl.
CPC .......... *A61B 5/14539* (2013.01); *A61B 5/443* (2013.01); *A61B 5/4875* (2013.01); *A61B 5/6833* (2013.01); *G01N 27/226* (2013.01); *G01N 33/4833* (2013.01); *A61B 2562/029* (2013.01); *A61B 2562/066* (2013.01); *A61B 2562/164* (2013.01); *A61H 2230/65* (2013.01)

(58) Field of Classification Search
CPC ..... A61B 5/443; A61B 5/4875; A61B 5/6833; A61B 2562/029; A61B 2562/066; A61B 2562/164; G01N 27/226; G01N 33/4833; A61H 2230/65
See application file for complete search history.

(56) References Cited

U.S. PATENT DOCUMENTS

| | | | |
|---|---|---|---|
| 6,762,609 | B2 | 7/2004 | Alanen et al. |
| 7,402,135 | B2 | 7/2008 | Leveque et al. |
| 7,569,762 | B2 | 8/2009 | Baum et al. |
| 8,541,745 | B2 | 9/2013 | Dickinson et al. |
| 8,663,106 | B2 | 3/2014 | Srivoric et al. |
| 8,947,382 | B2 | 2/2015 | Winkler et al. |
| 8,988,349 | B2 | 3/2015 | Alberth et al. |
| 10,022,277 | B2 | 7/2018 | Heil et al. |
| 10,115,051 | B2 | 10/2018 | Takashima et al. |
| 10,181,021 | B2 | 1/2019 | Venkatraman et al. |
| 2002/0180605 | A1 | 12/2002 | Ozguz et al. |
| 2008/0262376 | A1 | 10/2008 | Price |
| 2013/0200268 | A1* | 8/2013 | Rafferty ............... H04Q 9/00 250/206 |
| 2013/0333094 | A1* | 12/2013 | Rogers ............... A61B 34/76 340/407.1 |
| 2014/0275813 | A1 | 9/2014 | Stivoric et al. |
| 2016/0015962 | A1* | 1/2016 | Shokoueinejad Maragheh ........... A61F 13/00055 607/88 |
| 2016/0256070 | A1 | 9/2016 | Murphy et al. |
| 2017/0095166 | A1 | 4/2017 | Afzali-Ardakani et al. |
| 2018/0055359 | A1 | 3/2018 | Shamim et al. |
| 2018/0206729 | A1* | 7/2018 | Wang ............... A61B 5/282 |
| 2019/0011288 | A1* | 1/2019 | Nassar ............... A61B 5/01 |
| 2019/0046033 | A1* | 2/2019 | Gannon ............... G01K 1/024 |
| 2019/0069788 | A1 | 3/2019 | Coleman et al. |
| 2019/0117083 | A1 | 4/2019 | Wang et al. |
| 2019/0129066 | A1 | 6/2019 | Schoess et al. |
| 2020/0054218 | A1* | 2/2020 | Xi ............... A61B 5/015 |
| 2021/0022609 | A1* | 1/2021 | Rogers ............... A61B 5/0008 |
| 2021/0401359 | A1* | 12/2021 | Schoess ............... A61B 5/6801 |

FOREIGN PATENT DOCUMENTS

| | | |
|---|---|---|
| DE | 202014009247 | 3/2016 |
| EP | 0019154 | 5/1980 |
| WO | 2019086997 | 5/2019 |

OTHER PUBLICATIONS

Zuang et al., "The Use of a Capacitance Device to Evaluate the Hydration of Human Skin", J. Appl. Cosmetol., 15, 95-102, Jul.-Sep. 1997 (Year: 1997).*
Voldman et al., "Microfabrication in Biology and Medicine", Annu. Rev. Biomed. Eng., 01, 401-425, 1999 (Year: 1999).*
Farooqui et al., *Low Cost Inkjet Printed Smart Bandage for Wireless Monitoring of Chronic Wounds*, Scientific Reports, Jun. 29, 2016, 13 pages.
English Translation of CN203369905U (Patent Translate), 13 pages.
Tan et al., *A 1.2-V 8.3-nJ CMOS Humidity Sensor for RFID Applications*, IEEE Journal of Solid-State Circuits, vol. 48, No. 10, Oct. 2013, 9 pages.
Tan et al., *A 1.8V 11uW CMOS Smart Humidity Sensor for RFID Sensing Applications*, IEEE Asian Solid-State Circuits Conference, Nov. 14-16, 2011, Jeju, Korea, 4 pages.
English Translation of EP0019154A1 (Patent Translate), 8 pages.
English Translation of DE202014009247U1 (Patent Translate), 14 pages.
Machine translation of DE 1598910.

* cited by examiner

WEARABLE SENSOR AND METHOD OF FORMING THEREOF

CROSS-REFERENCE TO RELATED APPLICATIONS

This application claims the benefit of and priority to U.S. Patent Application Ser. No. 62/939,805 filed Nov. 25, 2019, entitled "WEARABLE SENSOR AND METHOD OF FORMING THEREOF", incorporated herein by reference in its entirety.

FIELD OF THE DISCLOSURE

The present disclosure relates to a wearable sensor having a flexible body. The present disclosure also relates to a method of forming such a wearable sensor.

BACKGROUND

Wearable sensors can be worn on the body and include sensor components for sensing a certain parameter of the body such as moisture or temperature. The output generated by the sensor components can be processed by some processing circuitry on or external to the wearable sensor, and then the processed output can be monitored or analysed by a computer. Sometimes, the wearable sensor is wired to a computer. Otherwise, the processed output can be transmitted wirelessly to a computer. The processed output can help a user decide if any changes should be made, for example, to their lifestyle in order to adjust the value of the body parameter being monitored.

SUMMARY OF DISCLOSURE

Wearable sensors are becoming increasingly popular in the healthcare and cosmetics industries. Recently, there has been a drive to adapt wearable sensors so that they are more suitable for everyday use by making them smaller in size and therefore less noticeable to the eye. In the present disclose, the wearable sensor is formed in a unitary flexible body to achieve this reduction in size. The wearable sensor (hereinafter also referred to as the "device") includes sensor components for sensing a certain parameter of human skin, a circuit for processing the output of the sensor components and an antenna for transmitting the processed output. In some wearable sensors, the sensor components, circuit and antenna are all embedded within the flexible body and the flexible body is configured to bend for maximum comfort to the user.

In accordance with a first aspect of the disclosure, there is provided a wearable sensor for measuring a parameter of human skin, comprising a flexible body comprising sensor components formed on, adjacent or within the flexible body and configured to generate a first signal indicative of the parameter of human skin; microfabricated processing circuitry formed within the flexible body, coupled to the sensor components and configured to process the first signal to produce a second signal; and an antenna, formed on, adjacent or within the flexible body, the antenna being coupled to the processing circuitry and configured to transmit the second signal to an external device.

By "flexible", it is meant that the body of the wearable sensor can bend without breaking. The flexible body is therefore capable of being flexed according to the contours of a user's skin in use, for example, when it is adhered to the user's face or another body part that is not entirely flat. Whilst the wearable sensor may be manufactured on a flat carrier substrate, in use, it can bend in order to accommodate for different curvatures without impacting upon its sensing capabilities. As well as being flexible, the wearable sensor can also be substantially transparent in order to minimise its appearance when adhered to a user's skin.

By "over", it will be appreciated that this refers to the orientation of the sensor as it is manufactured rather than any orientation of the sensor in use.

The flexible body of the wearable sensor is formed on a single substrate, i.e. each layer of the wearable sensor can be microfabricated or built on top of the previous layer. This has the advantageous effect of reducing the cost and complexity of the manufacturing process.

The flexible body may comprise a circuit layer, and the sensor components and the processing circuitry may be formed within the circuit layer. The sensor components may detect capacitance, using the user's skin as a dielectric when the wearable sensor is adhered thereto, or the sensor components may detect another parameter such as voltage. The sensor components many generate a first signal that is indicative of skin hydration, pH or temperature, for example. The circuit layer may comprise an oxide material.

The flexible body may comprise an antenna layer and the antenna may be formed on, adjacent or within the antenna layer. The antenna may be a near-field communications antenna. The antenna layer may comprise a plastic material such as polyimide, silicone, SU8 or LCP. When the antenna layer, or another layer of the wearable sensor, comprises a plastic material, the cost of producing the wearable sensor can be reduced compared with a silicon-based device.

The flexible body may comprise a first surface configured to be positioned on human skin and a second surface opposite the first surface. Sensor components may be formed on or adjacent the first surface, the antenna may be formed on or adjacent the second surface, and the processing circuitry may be formed therebetween.

In accordance with a second aspect of the disclosure, there is a provided a unitary integrated flexible sensor for measuring a parameter associated with a user's skin, the sensor comprising a flexible body having at least one layer being a microfabricated flexible material, the flexible body having a first surface configured for positioning on a user's skin, the sensor further comprising: at least one sensor component, positioned on or adjacent the first surface and configured to produce a first signal representative of the parameter associated with a user's skin; processing circuitry, coupled to the at least one sensor component, and configured to produce a second signal, suitable for transmission to a reading device; and an antenna, coupled to the processing circuitry, and configured to transmit the second signal to a reading device, the flexible body comprising a second surface, opposite the first surface, the antenna positioned on or adjacent the second surface; wherein the at least one sensor component, the processing circuitry and the antenna being microfabricated components.

In accordance with a third aspect of the disclosure, there is a provided a method of manufacturing a wearable sensor using microfabrication techniques, the method comprising: forming a flexible body; forming sensor components on, adjacent or within the flexible body; forming and processing circuitry within the flexible body; forming an antenna on, adjacent or within the flexible body; coupling the sensor components and processing circuitry such that, in use, a first signal generated by the sensor components that is indicative of a parameter of human skin is processable by the processing circuitry to produce a second signal; and coupling the antenna and the processing circuitry such that, in use, the antenna can receive the second signal from the processing circuitry and transmit the second signal to an external device.

Forming the flexible body may comprise forming an antenna layer having the antenna formed thereon or within and/or forming a circuit layer having the sensor components and the processing circuitry formed within. The antenna layer may be formed by spin coating or laminating a layer of plastic material on a glass carrier wafer. The circuit layer may be formed with a first surface configured to be positioned on human skin. Then, the flexible body may be removed from the glass carrier wafer by heating the layer of plastic material. A plurality of wearable sensors may be formed in the flexible body, for efficient manufacturing, and then the method may further comprise dicing the flexible body into individual wearable sensors.

In accordance with a fourth aspect of the disclosure, there is provided a system for acquiring a measure of humidity of human skin, the system comprising: a plurality of wearable sensors, wherein each wearable sensor provides a measure for the humidity of human skin and configured to be adherable to a user's face, wherein each wearable sensor comprises a flexible body comprising sensor components, microfabricated processing circuitry and an antenna, and wherein the outputs from the wearable sensors are configured to be processed by the microfabricated processing circuitry in order to determine a measure of humidity and transmitted to an external device in order to read out the measure of humidity.

In accordance with a fifth aspect of the disclosure, there is provided a system for acquiring a measure of pH of human skin, the system comprising: a plurality of wearable sensors, wherein each wearable sensor provides a measure for the pH of human skin and configured to be adherable to a user's face or body, wherein each wearable sensor comprises a flexible body comprising sensor components, microfabricated processing circuitry and an antenna, and wherein the outputs from the wearable sensors are configured to be processed by the microfabricated processing circuitry in order to determine a measure of pH and transmitted to an external device in order to read out the measure of pH.

In accordance with a sixth aspect of the disclosure, there is provided a system for acquiring a measure of temperature of human skin, the system comprising: a plurality of wearable sensors, wherein each wearable sensor provides a measure for the temperature of human skin and configured to be adherable to a user's face or body, wherein each wearable sensor comprises a flexible body comprising sensor components, microfabricated processing circuitry and an antenna, and wherein the outputs from the wearable sensors are configured to be processed by the microfabricated processing circuitry in order to determine a measure of temperature and transmitted to an external device in order to read out the measure of temperature.

In each of the above examples, advantages associated with one aspect of the disclosure may also be associated with another aspect of the disclosure if appropriate.

BRIEF DESCRIPTION OF THE DRAWINGS

Examples of the present disclosure will now be described, by non-limiting example only, with reference to the accompanying drawings, in which.

DETAILED DESCRIPTION

Wearable sensors for measuring parameters of the human body such as temperature that are currently available in the market are often bulky and can also be unsightly. As such, there have been certain endeavours in the industry to miniaturise wearable sensors.

In the present disclosure, improvements to wearable sensors are made by manufacturing the devices using microfabrication techniques. The overall solution results in a small, preferably transparent, device for measuring a parameter such as temperature or humidity that is capable of directly communicating back the measured parameter levels to an external device such as a smart phone. The resulting wearable sensor is advantageously low cost, flexible and has aesthetic appeal to allow for all day use.

The invention relates to a wearable sensor for detecting a parameter of human skin, for example, humidity, and it acquires a measured value, for example, capacitance, using sensing components in order to make the determination. For example, the wearable sensor determines moisture content against a reference capacitance value; the higher the measured capacitance is relative to the reference capacitance, the higher the moisture of the skin being measured. The sensor has a flexible plastic substrate and uses an antenna to communicate with an external device, for example, a mobile phone. Possible applications of this technology include measuring the moisture content of skin for cosmetic purposes and measuring moisture content of skin to measure how well a wound is healing using the medical patch.

Figure 1:
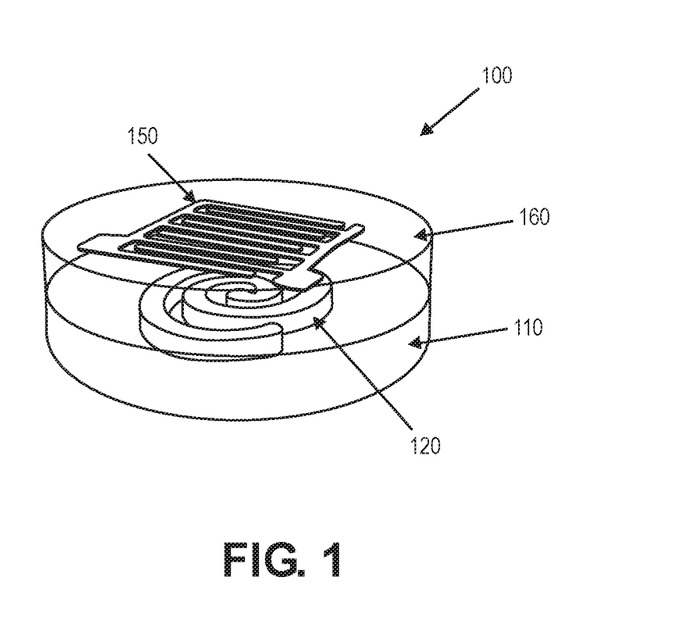
FIG. 1 is a perspective view of a wearable sensor in accordance with an example of the disclosure.

In one example of the disclosure, referring to FIG. 1, a perspective view of a wearable sensor or device 100 formed using micromachining techniques in accordance with an example of the disclosure is shown. The wearable device 100 of FIG. 1 is cylindrical in shape and may be deformed to a certain extent since the wearable sensor is flexible. In other examples, the device can be square or rectangular.

The structure of the wearable sensor 100 includes a near-field communications (NFC) antenna 120, which may be an RFID antenna, on one side and a capacitance sensor 150 on the other side. The side of the sensor with the NFC antenna 120 can be manufactured by spin coating a plastic layer or substrate 110 such as polyimide on a glass carrier substrate (not shown). The side with the capacitance sensor 150 may also have an adhesive (not shown) for sticking to skin, which allows the sensor to be a wearable device 100. Alternative substrates may include silicone, SU8 and LCP.

Plastic substrates such as polyimide are generally cheaper than silicon-based solutions. Further, there is a reduced need for packaging of the plastic substrates compared with silicon-based substrates. These factors make plastics substrate particularly suitable for wearable sensors. Although plastic substrates may not last as long as silicon-based substrates, there is no need for these wearable sensors to last a lifetime.

The NEC antenna 120 may be made of copper material. Although the shape of the NFC antenna 120 shown in FIG. 1. is a spiral coil, in other examples, it could be another shape such as a square coil or a hexagonal coil, with a different number of turns and having a different width and thickness. The NFC antenna 120 could also be used as a Bluetooth™ antenna rather than a RF Iii antenna in other examples, in which case the device may include a printed battery layer.

A capacitance sensor 150 as well as a capacitance-to-digital converter are provided. The capacitance-to-digital converter is not shown, but it can be formed by an organic semiconductor process such as indium gallium zinc oxide (IGZO) or a non-organic semiconductor process. The capacitance sensor 150 and capacitance-to-digital converter are built in an oxide layer 1.60 above the plastic substrate 110. Then, the plastic substrate 110 can be separated from the glass carrier substrate by heating such that the plastic layer is lifted off the glass substrate and the glass substrate does not form part of the resulting sensor. When the plastic substrate is manufactured having a plurality of sensors built thereon, a laser can then be used to dice the substrate into individual sensors.

In the specific example of FIG. 1. the wearable sensor 100 combines a plastic substrate 110 having an NFC antenna 120, which is a metal inductor process, with an IGZO process, which has metal interconnect on top. The top layer of metal interconnect forms an inter-digitated fringe capacitor constituting the capacitance sensor 150 and uses the skin as the dielectric in obtaining a measure of capacitance. The IGZO and other passive components are then used to form a capacitance-to-digital converter and NFC circuitry between the capacitance sensor 150 and NFC antenna 120. Rather than using IGZO, another option would be to use amorphous silicon or low temperature polysilicon.

The plastic layer 110, oxide dielectric 160, and IGZO are transparent or nearly transparent, only leaving the metals that are visual. This combination not only results in a practical sensor but is also an attractive end product that a user can wear all day. This is particularly useful for applications such as humidity sensing of a user's face since the wearable sensor is largely not visible without close inspection.

If silicon were used to implement the same wearable sensor as the example of FIG. 1, it would need to be attached to a PCB in order to form the NFC antenna. However, this would limit the flexibility of the wearable sensor overall. Alternatively, a redistribution layer could be applied to the back of the silicon and through-silicon vias could be used to attach the antenna, but this would result in a bulky solution that is not necessarily suitable for a flexible wearable sensor.

Figure 2:
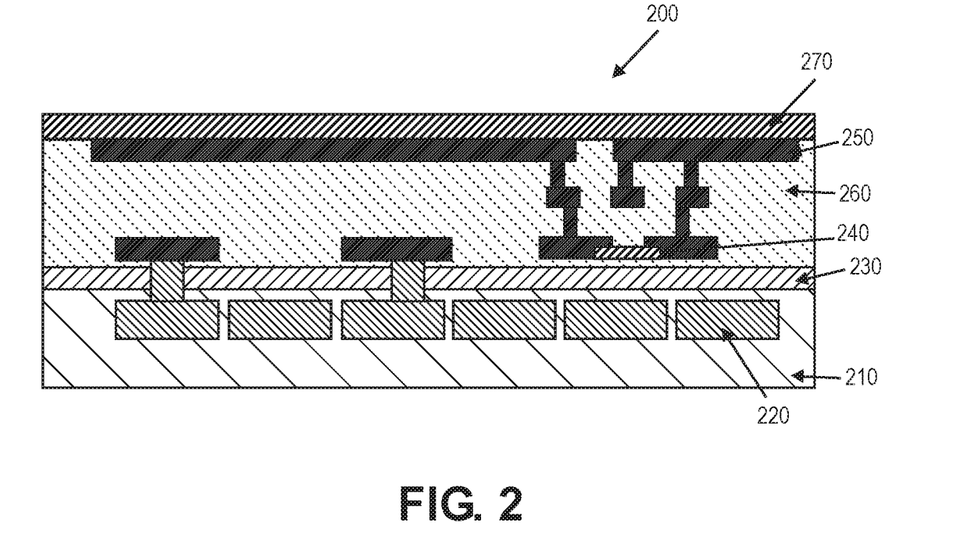
FIG. 2 is a cross-sectional view of a wearable sensor in accordance with another example of the disclosure.

FIG. 2 shows a cross-section through a wearable sensor 200 formed using micromachining techniques in accordance with an example of the disclosure.

The wearable sensor 200 comprises a polyimide layer 210 and an oxide layer 260. The polyimide layer 210 and oxide layer 260 together form a flexible body of the device. Embedded within the polyimide layer 210 is a NFC antenna 220 and an optional magnetic layer 230. Embedded within the oxide layer 260 is processing circuitry made of IGZO 240 and capacitance sensing components 250. Since the capacitance sensing components 250 are embedded within the oxide layer 260, this is the side of the wearable sensor 200 that is configured to be placed close to the user's skin. An adhesive layer 270 applied on the oxide layer 260 allows the wearable sensor to be adhered to the user's skin.

In use, the wearable sensor 200 is adhered to the user's skin via adhesive layer 270. Once adhered, the wearable sensor 200 uses the dielectric constant of human skin (or the dielectric constant of a different external material to the sensor) together with a value of sensed capacitance from the capacitance sensing component 250 and processes these values using processing circuitry 240. Once processed by processing circuitry 240, the processed value can be transmitted to an external device via antenna 220 so that it can be read out, monitored or analysed.

Figure 3:
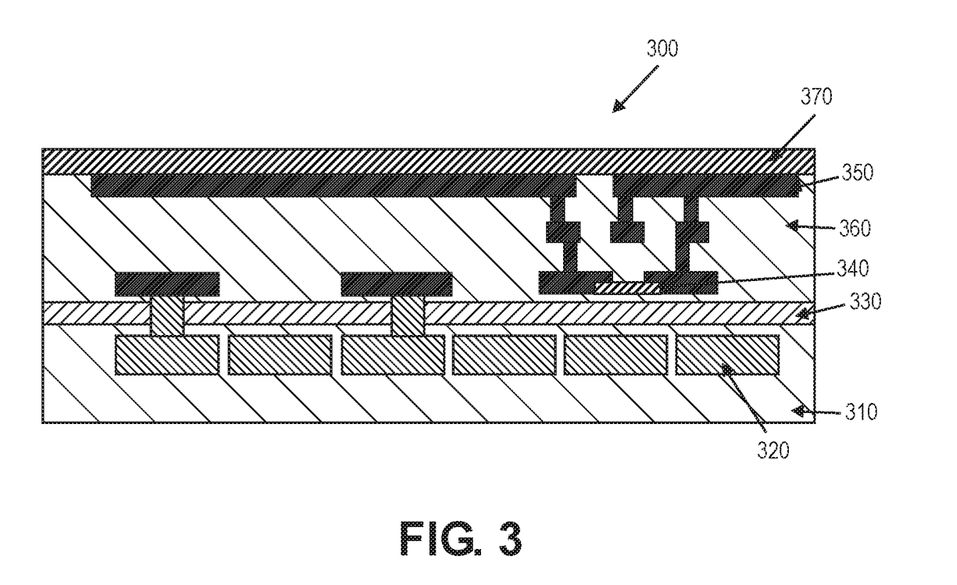
FIG. 3 is a cross-sectional view of a wearable sensor in accordance with another example of the disclosure.
Figure 4:
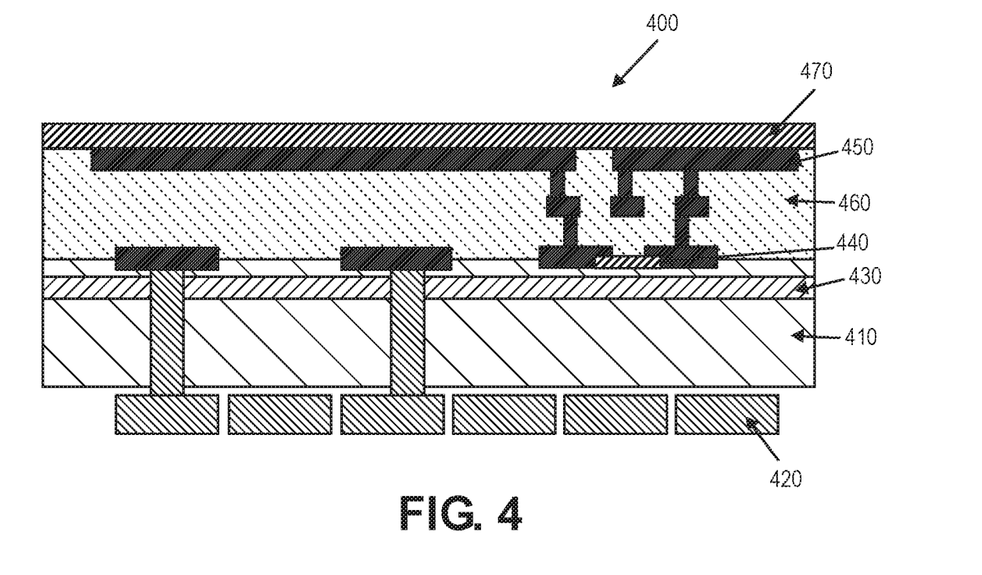
FIG. 4 is a cross-sectional view of a wearable sensor in accordance with another example of the disclosure.
Figure 5:
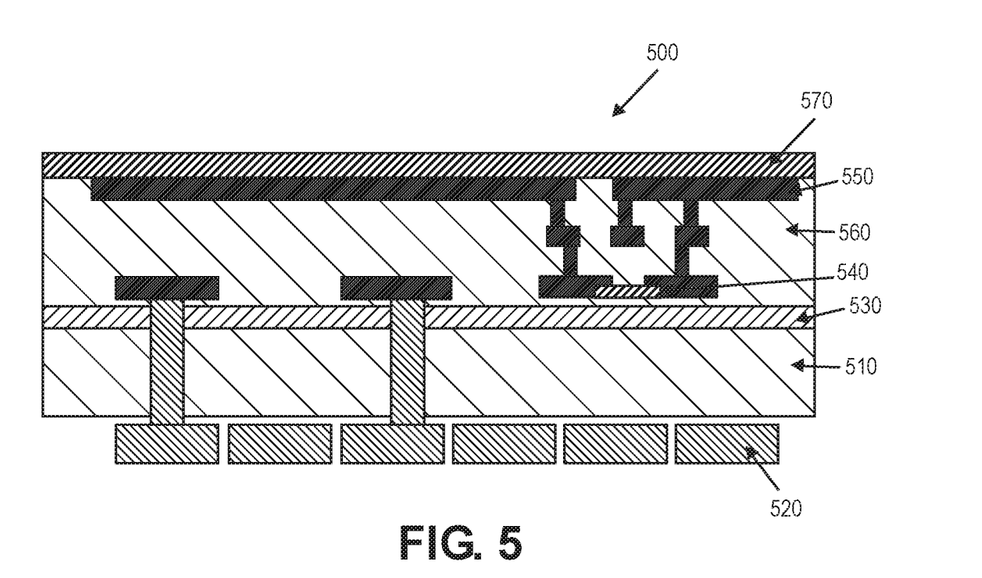
FIG. 5 is a cross-sectional view of a wearable sensor in accordance with another example of the disclosure.

The wearable sensor 200 of FIG. 2 is a preferred example, in which a flexible hydration sensor has an embedded RFID antenna in a flexible polyimide substrate and the sensor components/processing circuitry are built thereon within an oxide layer. However, other arrangements of the structure of the wearable sensor are shown in FIGS. 3-5. Technical effects and advantages associated with the example of FIG. 2 may also apply to the examples of FIGS. 3-5.

In FIG. 3, instead of a polyimide layer and an oxide layer, the flexible body of the wearable sensor 300 comprises only a polyimide layer 310. The use of a single material as the substrate simplifies the manufacturing process and, again, using a plastic material reduces the overall cost of the wearable sensor 300.

FIGS. 4 and 5 are similar to the examples of FIGS. 2 and 3, respectively, except the antenna 420, 520 is shown to be outside of the main body of the device, i.e. in a non-embedded arrangement, using the metallisation layer as a connection point for attachment.

Figure 6:
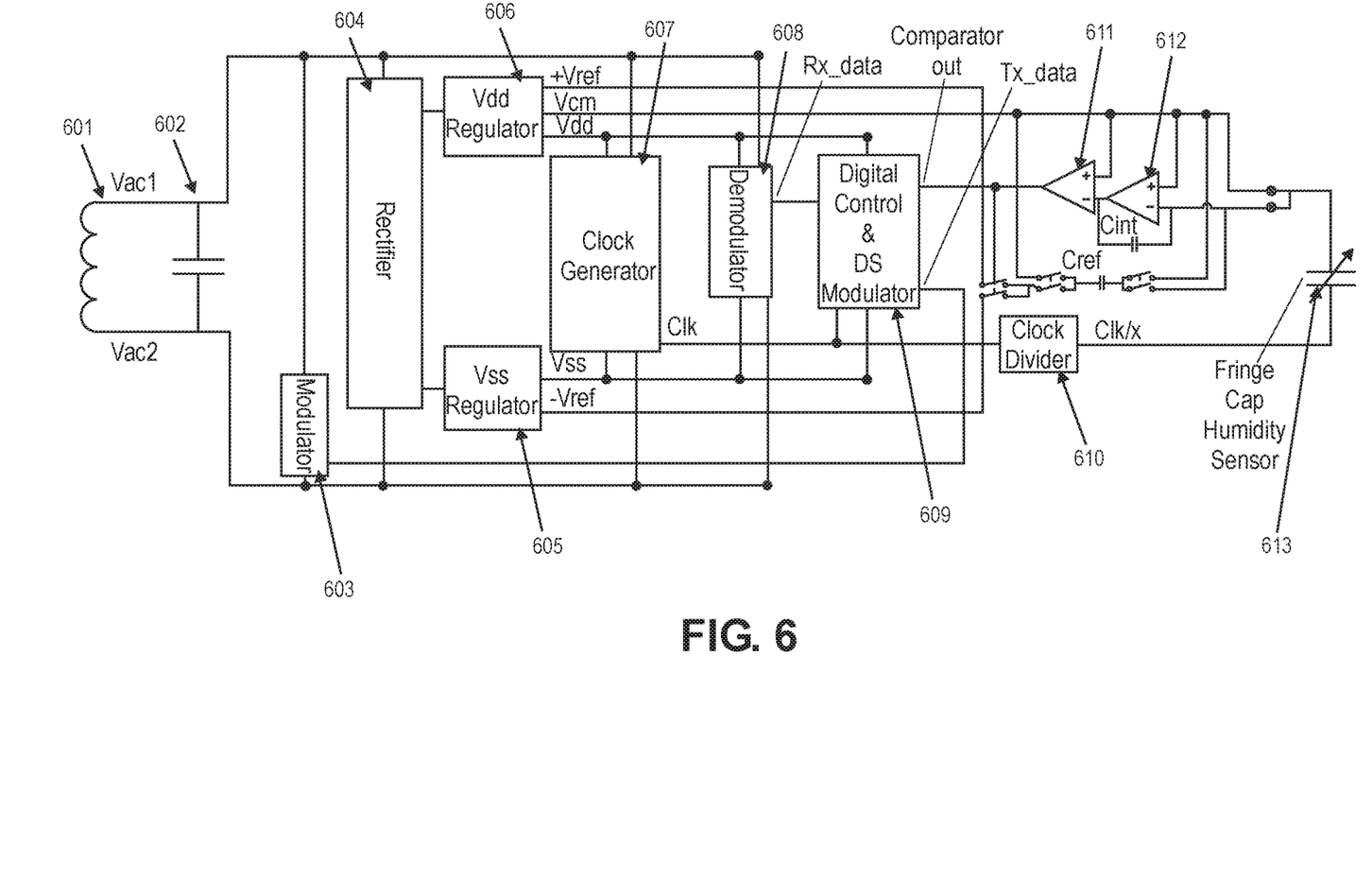
FIG. 6 shows a schematic of the sensor and processing circuitry in accordance with an example of the present disclosure.

FIG. 6 shows an example schematic of the sensor and processing circuitry useable in the wearable sensor of any of FIGS. 1-5. Included in the sensor and processing circuitry is a resonant circuit (comprising inductor 601 and capacitor 602), a modulator 603, a rectifier 604, a VSS regulator 605, a VDD regulator 606, a voltage reference (not shown) a clock generator 607, a demodulator 608, a digital control and DS/SD modulator 609, a clock divider 610, two comparators 611, 612 and a capacitance sensor 613. The input from the capacitance sensor 613 is compared with a nominal value of capacitance produced and regulated by the other circuit components of the processing circuitry. In other examples, rather than a capacitance, another type of sensor collecting an input signed may be used, such as a voltage sensor. In yet further examples, there is an option to switch between an array of temperature sensors or capacitance sensors.

A method of fabricating the wearable sensor 100 will now be described with reference to FIGS. 7A-7I.

Figure 7A:
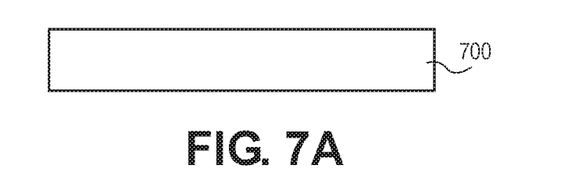
FIG. 7A schematically illustrates a carrier wafer at an initial phase of a fabrication process for an example wearable sensor of the disclosure.

In FIG. 7A, a carrier wafer 700 is provided, upon which the device can be built using microfabrication processes. In some examples, the carrier wafer can be an 8-inch glass wafer. Alternatively, it may be made of polycarbonate or quartz, or any combination of the above-mentioned materials. The carrier wafer 700 provides support to the device that is built thereupon. However, at the end of the process, the glass carrier wafer is removed so that it does not form a part of the device.

Figure 7B:
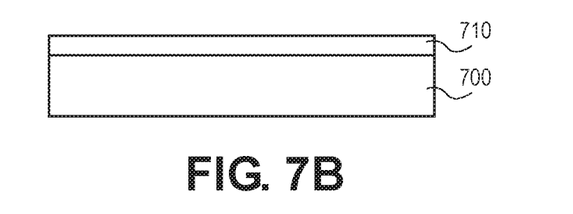
FIG. 7B shows the carrier wafer after partial formation of a plastic layer.

FIG. 7B shows the first step in the fabrication process of the device, which involves spin coating a layer of polyimide 710 onto the glass carrier substrate 700. This initial layer of polyimide may be around 0.1 mm thick.

Figure 7C:
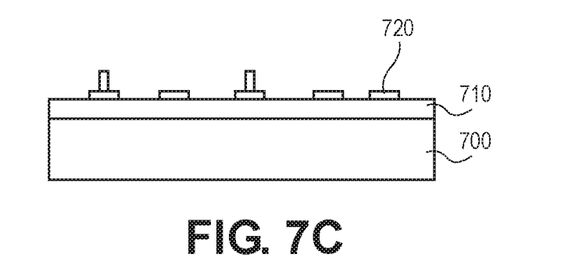
FIG. 7C shows the carrier wafer after formation of an antenna above the partial plastic layer.

An antenna 720 is then formed on top of the polyimide 710 in FIG. 7C. The antenna 720 may be an NFC antenna 720 made of copper. It is formed in a spiral shape over the polyimide 710. Alternative materials for the antenna could be copper or gold; choice of metal material can be based on resistance/inductance or can simply be for aesthetic reasons.

Figure 7D:
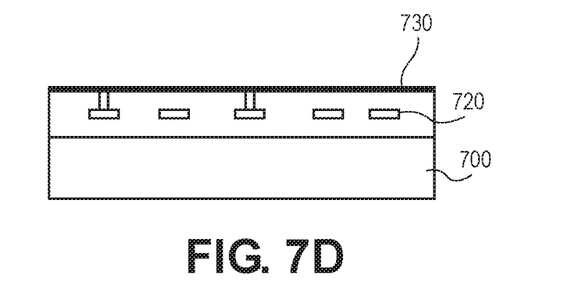
FIG. 7D shows the carrier wafer after further formation the plastic layer to embed the antenna and formation of an insulating layer above the antenna.
Figure 7E:
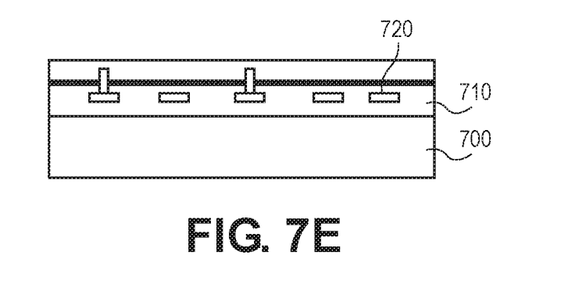
FIG. 7E shows the carrier wafer after further formation of the plastic layer to embed the insulating layer.

In FIG. 7D, more polyimide 710 is spun onto the antenna 720 to seal the antenna components within the polyimide 710. Then, a metallisation layer 730, or redistribution layer, is formed over the polyimide. The metallisation layer 730 provides the functionality of providing metal contact between the NFC antenna 720 and the capacitance sensor components to be built in the following method steps. In FIG. 7E, more polyimide 710 is spun onto the metallisation layer 730 in order to embed it within the polyimide 710. The total thickness of the polyimide 710 may be around <50 um but >0.5 um. One benefit of spin coating the polyimide 710 is that it creates a uniform surface upon which other circuit components may be built.

Figure 7F:
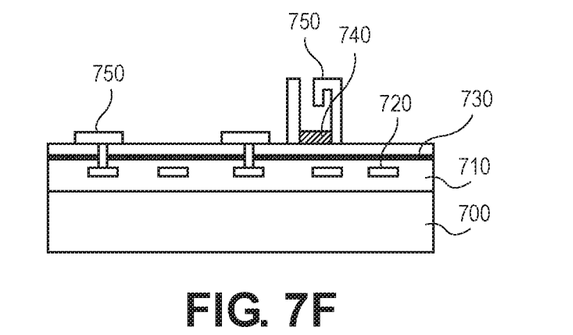
FIG. 7F shows the carrier wafer after deposition of processing circuitry and partial deposition of the sensor components above the plastic layer.

Next, in FIG. 7F, processing circuitry made of IGZO 740 and capacitance sensor components 750 made of indium tin oxide (ITO) or Aluminium (AL) or Copper (Cu) or Silver (Ag) are built upon the polyimide layer 710. FIG. 7F shows a top gate TFT device but similarly a bottom gate device can be formed. The IGZO 740 and capacitance sensor components 750 can be deposited using microfabrication techniques. For example, the IGZO 740 and capacitance sensor components 750 can be deposited using pulsed laser deposition (PLD) or another low-temperature deposition technique.

Figure 7G:
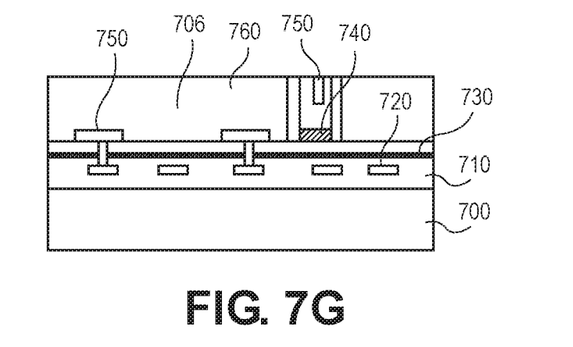
FIG. 7G shows the carrier wafer after formation of an oxide layer to embed the processing circuitry and sensor components.

Then, in FIG. 7G, an oxide layer 760 is spun onto the IGZO 740 and capacitance sensor components 750 so as to embed them. A suitable oxide material might be copper oxide (CuO), nitrogen oxide (NiO), zinc oxide (ZnO), Silicon oxide (SiO) or aluminium oxide (AlO). The thickness of the oxide layer 760 may be of the same order as the polyimide layer 710, i.e. <50 um but >0.5 um, such that the overall device may be around 1 mm thick.

Figure 7H:
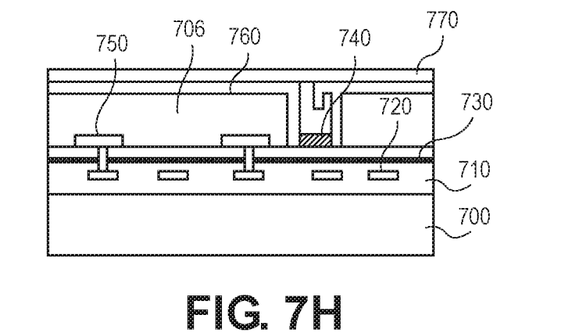
FIG. 7H shows the carrier wafer after further deposition of sensor components above the oxide layer and application of an adhesive over the oxide layer and sensor components.

In FIG. 7H, an adhesive layer 770 is applied over the capacitance sensor components 750 and oxide layer 760 so as to allow the wearable sensor to be adhered to a skin of a user. A waterproof and breathable adhesive that allows for movement of moisture is preferred. Additionally or alternatively, the adhesive layer 770 may have small laser cut-out holes in order to make it breathable. In some examples, the entire sensor may have holes from the base to the top to allow for breathability and water transfer. In other examples a layer of PDMS can also be applied to protect it from contaminants prior to the formation of holes. A layer of Hydrogel Silicone can then be applied to both sides of the singulated die to improve biocompatibility.

Figure 7I:
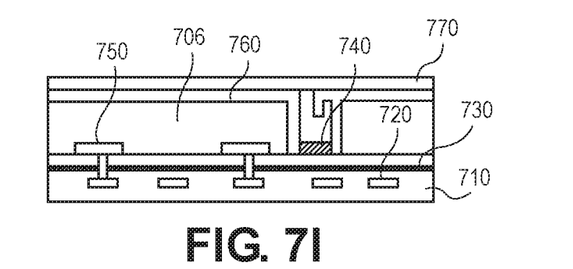
FIG. 7I shows the wearable sensor after removal from the carrier wafer.

Finally, in FIG. 7I, the glass carrier wafer 700 is separated from the wearable sensor by using a laser to heat the interface between the glass carrier wafer and the polyimide layer 710 such that the polyimide layer 710 melts slightly and is lifted off from the glass carrier wafer 700.

Once lifted from the glass carrier wafer, the individual wearable sensors can be stuck onto a sticky sensor sheet, adhesive-side down. This way, they are ready to be peeled off for use as needed, as will be described in further details with reference to the systems of FIGS. 8-10.

Figure 8:
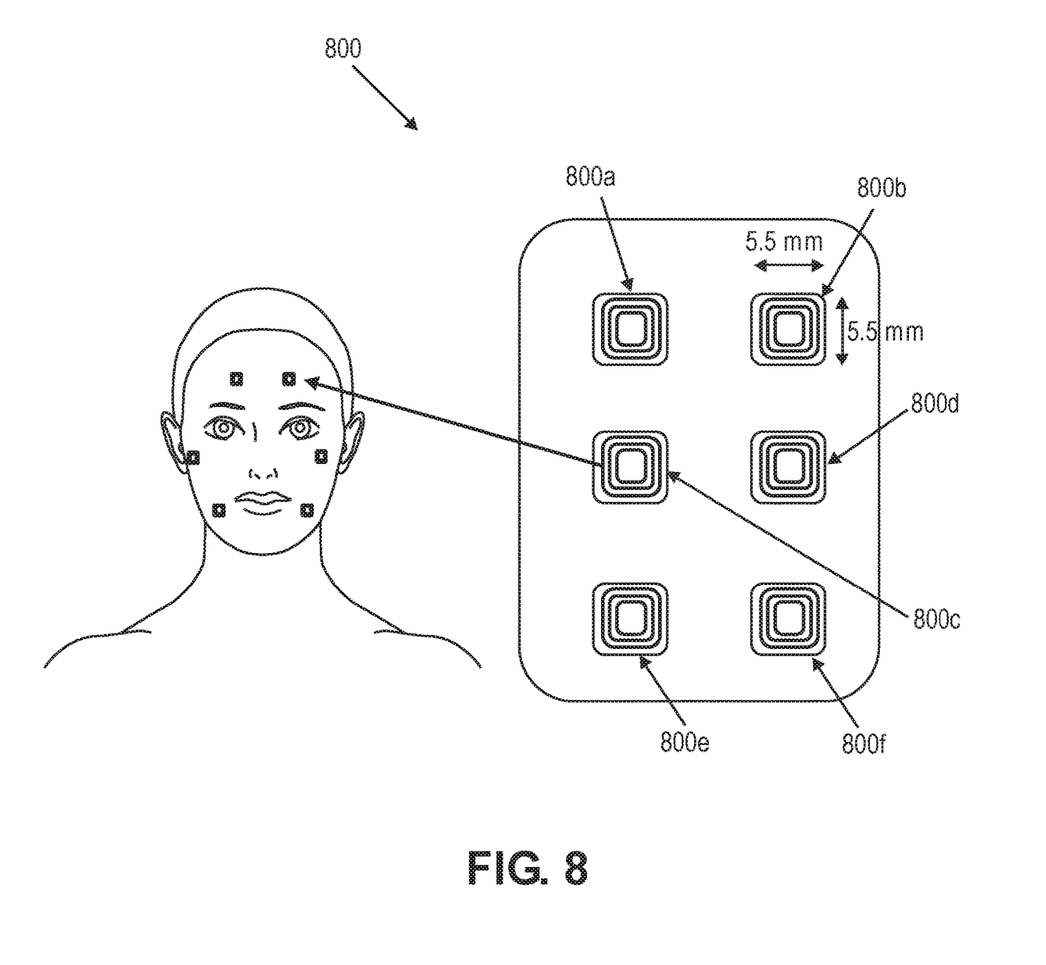
FIG. 8 is a system for acquiring a measure of a parameter of human skin in accordance with another example of the disclosure.

In FIG. 8, a system 800 for acquiring a measure of humidity of human skin is shown. The system 800 has six individual wearable sensors, 800a, 800b, 800c, 800d, 800e, 800f, and each wearable sensor is configured to provide a measure for the humidity of human skin and configured to be adhered to a user's face. Each individual wearable sensor, 800a, 800b, 800c, 800d, 800e, 800f, may be of the type shown in FIG. 2, having a flexible body comprising capacitance sensor components, microfabricated processing circuitry and an antenna.

The outputs from the wearable sensors are configured to be processed by the microfabricated processing circuitry in order to determine a measure of humidity and transmitted to an external device in order to read out the measure of humidity.

Skin care consumable manufacturers may desire to measure the effect of their skin care products on a customer's skin to allow for direct feedback of the effects of the product or to suggest an alternative product. The disclosure of FIG. 8 allows this direct feedback in the form of system 800, i.e. a sticky sensor sheet, upon which six wearable sensors are provided.

Figure 9:
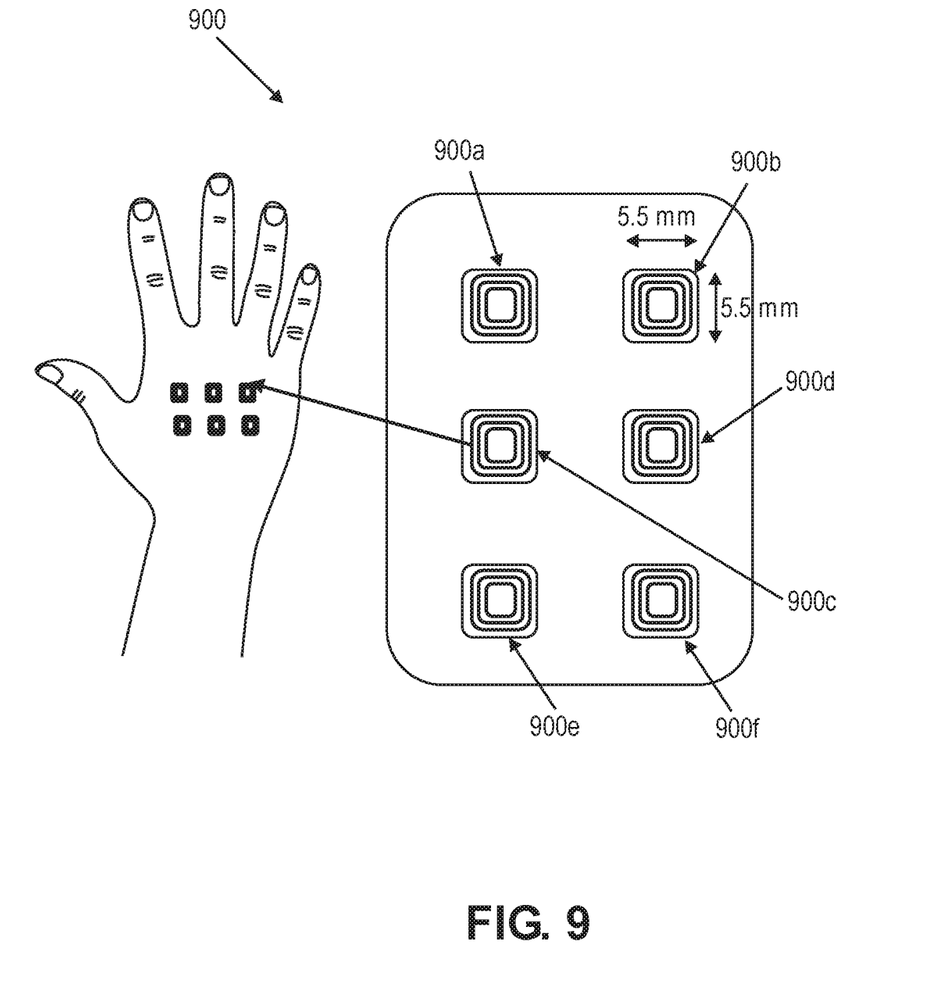
FIG. 9 is system for acquiring a measure of a parameter of human skin in accordance with another example of the disclosure.

In FIG. 9, a system 900 for acquiring a measure of pH of human skin is shown. The system 900 has six wearable sensors, 900a, 900b, 900c, 900d, 900e, 900f, and each wearable sensor is configured to provide a measure for the pH of human skin and configured to be adhered to the back of a user's hand. These individual wearable sensors, 900a, 900b, 900c, 900d, 900e, 900f, may have a flexible body comprising voltage sensor components, microfabricated processing circuitry and an antenna. Using voltage measurements from the sensor component, the processing circuitry converts these measurements into an output that is compared with a nominal voltage value and then the process output is transmitted to an external device via the antenna. If the process value differs too much from the nominal value, the user may be alerted and advised to apply some cream or another treatment to their hand in order to adjust the pH value. Again, the wearable sensors, 900a, 900b, 900c, 900d, 900e, 900f, are used to provide a user with direct feedback in a system that can be worn by the user all day without inconvenience. A silicon based NFC-to-Bluetooth converter device may be assembled on top of the flexible device to allow for constant communication. The method of sticking could be using glue, inserting the Bluetooth device into a pouch built into the flex sensor or using a snap button for easy placement and removal.

Figure 10:
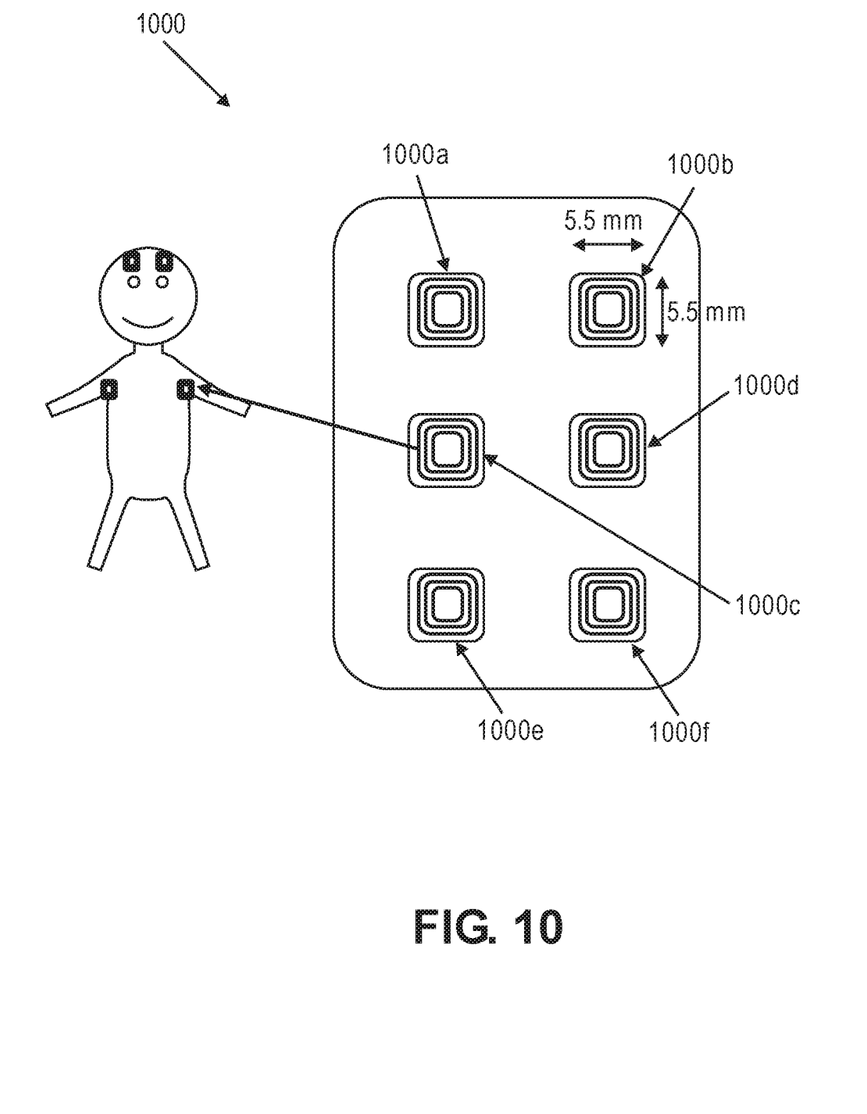
FIG. 10 is system for acquiring a measure of a parameter of human skin in accordance with another example of the disclosure.

In FIG. 10, a system 1000 for requiring a measure of temperature of human skin is shown. The system 1000 has six wearable sensors, 1000a, 1000b, 1000c, 1000d, 1000e, 1000f, and each wearable sensor is configured to adhere to various parts of the body where temperature remains consistent, for example, on the forehead or below the armpits. Each variable sensor, 1000a, 1000b, 1000c, 1000d, 1000e, 1000f, measures voltage in order to provide an indication of temperature.

Apart from the above mentioned systems that detects the parameters of capacitance and voltage, and which provide an indication of hydration, pH and temperature of human skin, it is envisaged that other systems that are configured to detect other parameters and which provides an indication of other parameters of human skin are also covered by the disclosure. For example, in an organic gas sensor, environmental gases may cause changes in thermal voltage. In other examples, biosensors may be used to detect chemical substances, for example, using organic transistors. In some systems according to examples of the disclosure, a combination of different wearable sensors may be used to determine an indication of a parameter of human skin.

The disclosure above has been described in the context of a flexible wearable sensor, but it will be appreciated that other implementations are possible. For example, it is envisaged that wearable sensor having a non-flexible body but sharing the other features as described above can also produce some or all of the effects of the wearable sensors having a flexible body.

Variations and modifications will be apparent to the skilled person, such as equivalent and other features which are already known and which may be used instead of, or in addition to, features described herein. Features that are described in the context of separate aspects or examples may be provided in combination in a single aspect or example. Conversely, features which are described in the context of a single aspect or example may also be provided separately or in any suitable sub-combination.

What is claimed is:

1. A wearable device, comprising:
    a flexible body comprising:
        sensor components configured to:
            detect capacitance of human skin; and
            generate, based on the capacitance, a first signal indicative of an attribute of the human skin;
        microfabricated processing circuitry formed within the flexible body, the microfabricated processing circuitry being coupled with the sensor components and configured to process the first signal to produce a second signal; and
        an antenna coupled with the microfabricated processing circuitry and configured to transmit the second signal to an external device,
    wherein the flexible body comprises a first surface configured to be positioned on the human skin and a second surface opposite the first surface, and
    wherein the sensor components are formed on or adjacent the first surface, the antenna is formed on or adjacent the second surface, and the microfabricated processing circuitry is formed between the first surface and the second surface.

2. The wearable device of claim 1, wherein the flexible body comprises a circuit layer on or adjacent the first surface, and wherein the sensor components and the microfabricated processing circuitry are formed within the circuit layer.

3. The wearable device of claim 2, wherein the circuit layer comprises an oxide material.

4. The wearable device of claim 1, wherein the flexible body comprises an antenna layer on or adjacent the second surface, and wherein the antenna is formed on, adjacent or within the antenna layer.

5. The wearable device of claim 4, wherein the antenna layer comprises a plastic material.

6. The wearable device of claim 1, wherein the flexible body is substantially transparent.

7. The wearable device of claim 1, wherein the antenna is a near-field communications antenna.

8. The wearable device of claim 1, wherein the sensor components are further configured to detect voltage.

9. The wearable device of claim 1, wherein the first signal is ene of hydration of the human skin.

10. A unitary integrated flexible sensor, comprising:
    a flexible body having at least one layer being a microfabricated flexible material, the flexible body having a first surface configured for positioning on skin of a subject;
    at least one sensor component configured to:
        detect capacitance of the skin; and
        produce, based on the capacitance, a first signal representative of an attribute of the skin;
    processing circuitry coupled to the at least one sensor component and configured to produce, based on the first signal, a second signal suitable for transmission to a reading device; and
    an antenna coupled to the processing circuitry and configured to transmit the second signal to the reading device,
    wherein the flexible body comprises a second surface opposite the first surface,
    the at least one sensor component, the processing circuitry, and the antenna being microfabricated components,
    wherein the at least one sensor component is formed on or adjacent the first surface, the antenna is formed on or adjacent the second surface, and the processing circuitry is formed between the first surface and the second surface.

11. A method of manufacturing a wearable device, comprising:
    forming a flexible body having a first surface and a second surface opposite the first surface, the first surface being configured to be positioned on human skin;
    forming sensor components on or adjacent the first surface, the sensor components being configured to detect capacitance;
    forming an antenna on or adjacent the second surface;
    forming processing circuitry between the first surface and the second surface;
    coupling the sensor components and the processing circuitry to cause a first signal generated by the sensor components to be processable by the processing circuitry to produce a second signal, wherein the first signal is indicative of a parameter of the human skin; and
    coupling the antenna and the processing circuitry to cause the antenna to receive the second signal from the processing circuitry and further cause the antenna to transmit the second signal to a device that is external to the wearable device.

12. The method of claim 11, wherein forming the antenna comprises spin coating a layer of plastic material on a glass carrier wafer.

13. The method of claim 12, further comprising removing the flexible body from the glass carrier wafer by heating the layer of plastic material.

14. The method of claim 11, further comprising forming a plurality of wearable sensors on or adjacent the first surface.

* * * * *

UNITED STATES PATENT AND TRADEMARK OFFICE
CERTIFICATE OF CORRECTION

| | | |
|---|---|---|
| PATENT NO. | : 11,974,856 B2 | Page 1 of 1 |
| APPLICATION NO. | : 17/064587 | |
| DATED | : May 7, 2024 | |
| INVENTOR(S) | : Fergus Downey et al. | |

It is certified that error appears in the above-identified patent and that said Letters Patent is hereby corrected as shown below:

On the Title Page

Item (72) The second inventor city reads:
Raheen

Should read:
--Limerick--

Signed and Sealed this
Second Day of July, 2024

Katherine Kelly Vidal
*Director of the United States Patent and Trademark Office*